(12) United States Patent
Taimisto et al.

(10) Patent No.: US 7,519,410 B2
(45) Date of Patent: Apr. 14, 2009

(54) LA PLACIAN ELECTRODE (75) Inventors: Miriam H. Taimisto, San Jose, CA (US); David E. Haines, Charlottesville, VA (US); Steven Yee, Sunnyvale, CA (US); Steven Ha, Hayward, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 11/678,511

(22) Filed: Feb. 23, 2007

(65) Prior Publication Data
US 2007/0135700 A1   Jun. 14, 2007

Related U.S. Application Data

(63) Continuation of application No. 11/177,525, filed on Jul. 7, 2005, now Pat. No. 7,197,349, which is a continuation of application No. 10/318,655, filed on Dec. 12, 2002, now Pat. No. 6,922,579.

(51) Int. Cl.
*A61B 5/04* (2006.01)
*A61B 18/14* (2006.01)

(52) U.S. Cl. .............. 600/374; 606/41; 606/48; 606/50; 607/122

(58) Field of Classification Search .......... 600/374
See application file for complete search history.

(56) References Cited

U.S. PATENT DOCUMENTS

| | | | |
|---|---|---|---|
| 3,920,021 A | 11/1975 | Hiltebrandt | |
| 4,301,802 A * | 11/1981 | Poler | 606/48 |
| 4,548,207 A | 10/1985 | Reimels | |
| 4,674,499 A | 6/1987 | Pao | |
| 4,784,161 A | 11/1988 | Skalsky et al. | |
| 4,848,352 A | 7/1989 | Pohndorf et al. | |
| 4,960,134 A | 10/1990 | Webster, Jr. | |
| 5,125,928 A | 6/1992 | Parins et al. | |
| 5,277,696 A | 1/1994 | Hagen | |
| 5,363,861 A | 11/1994 | Edwards et al. | |
| 5,395,327 A | 3/1995 | Lundquist et al. | |
| 5,398,683 A | 3/1995 | Edwards et al. | |
| 5,456,664 A | 10/1995 | Heinzelman et al. | |
| 5,531,686 A | 7/1996 | Lundquist et al. | |
| 5,582,609 A | 12/1996 | Swanson et al. | |
| 5,718,701 A | 2/1998 | Shai et al. | |

(Continued)

OTHER PUBLICATIONS

Poole, Wayne F., et al., "Method for Modelling the Potential Sensed by a Concentric Multi-Ring Electrode Set from a Moving Depolarization Wave," IEEE Engineering in Medicine & Biology Society 11Annual International Conference—1297 CH-2770-6/89/0000-1297 C 1989.

*Primary Examiner*—Lee S Cohen
(74) *Attorney, Agent, or Firm*—Vista IP Law Group LLP (57) ABSTRACT

A medical probe for mapping is provided. The medical probe includes an elongated member, a first mapping ring electrode mounted to the elongated member, and a second mapping ring electrode mounted to the elongated member. The first and second mapping ring electrodes are electrically insulated from each other. The second mapping ring electrode is located substantially concentric to the first mapping ring electrode, and is coaxially surrounding the first mapping ring electrode.

13 Claims, 9 Drawing Sheets

U.S. PATENT DOCUMENTS

| | | |
|---|---|---|
| 5,782,760 A | 7/1998 | Schaer |
| 5,810,802 A | 9/1998 | Panescu et al. |
| 5,836,875 A | 11/1998 | Webster et al. |
| 5,891,088 A | 4/1999 | Thompson et al. |
| 5,967,976 A | 10/1999 | Larsen et al. |
| 6,001,095 A | 12/1999 | de la Rama et al. |
| 6,033,378 A | 3/2000 | Lundquist et al. |
| 6,064,905 A | 5/2000 | Webster, Jr. et al. |
| 6,134,463 A | 10/2000 | Wittkampf et al. |
| 6,379,350 B1 | 4/2002 | Sharkey et al. |
| 6,405,067 B1 | 6/2002 | Mest et al. |
| 6,477,396 B1 | 11/2002 | Mest et al. |
| 6,922,579 B2 | 7/2005 | Taimisto et al. |
| 7,197,349 B2 * | 3/2007 | Taimisto et al. ............ 600/374 |

* cited by examiner

FIG. 23

LA PLACIAN ELECTRODE

RELATED APPLICATION DATA

This application is a continuation of U.S. patent application Ser. No. 11/177,525, filed Jul. 7, 2005, now U.S. Pat. No. 7,197,349, which is a continuation of U.S. patent application Ser. No. 10/318,655, filed Dec. 12, 2002, now U.S. Pat. No. 6,922,579.

FIELD OF THE INVENTION

The present invention is directed to medical probes, and more particularly, to medical probes for ablation of body tissue.

BACKGROUND

Physicians make use of catheters today in medical procedures to gain access into interior regions of the body to ablate targeted tissue areas. It is important for the physician to be able to precisely locate the catheter and control its emission of energy within the body during tissue ablation procedures.

For example, in electrophysiological therapy, ablation is used to treat cardiac rhythm disturbances. During these procedures, a physician steers a catheter with a distally mounted ablating element through a main vein or artery into the interior region of the heart. The physician locates the ablating element adjacent the cardiac tissue to be treated, and directs energy from the ablating element into the tissue to form a lesion thereon. Typically, the determination of a target site and the ablation of the target site are performed by a single catheter, which consists of an ablation eye electrode mounted at the tip of the catheter, and a mapping ring electrode mounted distal to the ablation electrode. This and similar catheter tip designs are described in U.S. Pat. No. 6,134,463.

It has been found that current catheter tip designs do not always provide a physician with enough resolution to accurately identify ablation site, causing the physician to perform multiple ablations in several areas. In particular, current catheter tips may detect far field electrical activity, which can negatively affect the detection of local electrical activity. This results in extended operation time and, often times, unnecessary tissue ablation. Furthermore, current catheter tips may include a temperature sensor located behind (or proximal) to the eye electrode for measuring the temperature of the tissue being ablated. Because the eye electrode is in between the temperature sensor and the tissue, and/or because the temperature sensor is not directly placed against the tissue, the temperature measurement obtained by the sensor may not be accurate.

As such, there is a need for a catheter tip that is capable of precisely measuring electrical signals from a heart in order to accurately determine an ablation site. Such catheter tip should also be able to accurately ablate a target tissue at the ablation site, and allow a sensor (in one is used) to accurately measure a characteristic of the tissue being ablated.

SUMMARY OF THE INVENTION

According to a first aspect of the present invention, a catheter tip having a first mapping ring electrode and a second mapping ring electrode is provided. The second ring electrode is concentrically located outside the first ring electrode, and is electrically insulated from the first ring electrode. In the preferred embodiment, each of the first and second ring electrodes is electrically coupled to at least one wire for transmitting signals sensed by the respective first and second ring electrodes. Although the present inventions should not be so limited, with respect to the mapping functions, the concentric electrode arrangement can increase mapping resolution. The catheter tip can be a part of, or connected to, the distal end of an elongated member of an catheter or other medical devices. The distal end of the elongated member can have any shape, such as straight, curvilinear, or three-dimensional.

In a preferred embodiment, the distal ends of the first and second ring electrodes form a planar surface that is substantially perpendicular to an axis of the elongated member. Alternatively, the planar surface can be at an angle relative to the axis of the elongated member. The distal ends of the first and second ring electrodes can also form a non-planar surface, such as a surface with a parabolic or an angular profile.

The catheter tip may optionally include a sensor located within the bore of the ring electrode. In a preferred embodiment, the sensor is a thermal sensor that senses the temperature of a body tissue during an ablation process. However, the sensor can also be of the type that senses a current, an impedance, a pressure, or other characteristics of a body tissue. One or more of the sensor can also be secured along a body of the catheter.

Other and further aspects and features of the invention will be evident from reading the following detailed description of the drawings, which is intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
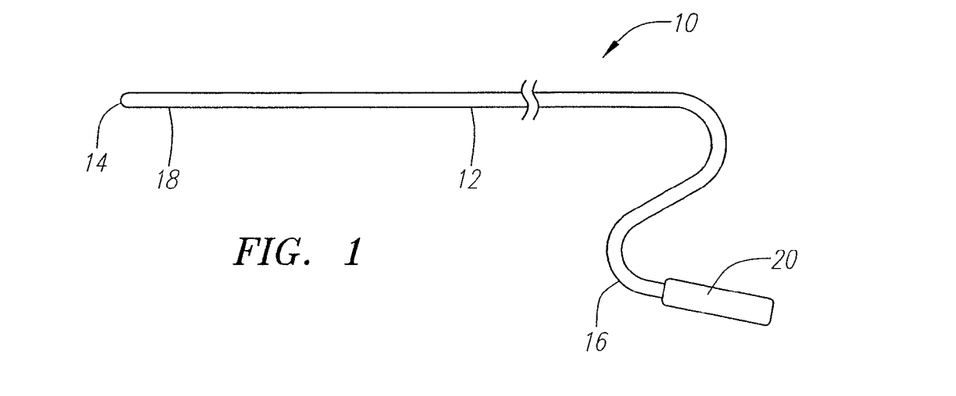
FIG. 1 is a plan view of a preferred embodiment of a catheter in accordance with the present invention.

Turning to the drawings, FIG. 1 illustrates an exemplary embodiment of an ablation/mapping catheter 10 constructed in accordance with the present inventions. The catheter 10 includes an catheter body 12 having a proximal end 16, a distal end 18, and a lumen (not shown) extending between the proximal end 16 and the distal end 18. The distal end 18 of the catheter body 12 includes a catheter tip 14, which carries two ring electrodes 22 and 24 (shown in FIG. 6) for mapping and/or ablation of target tissue. The electrodes will be described in further detail below. The catheter 10 optionally includes a handle 20 mounted on the proximal end 16 of the catheter body 12.

Figure 2:
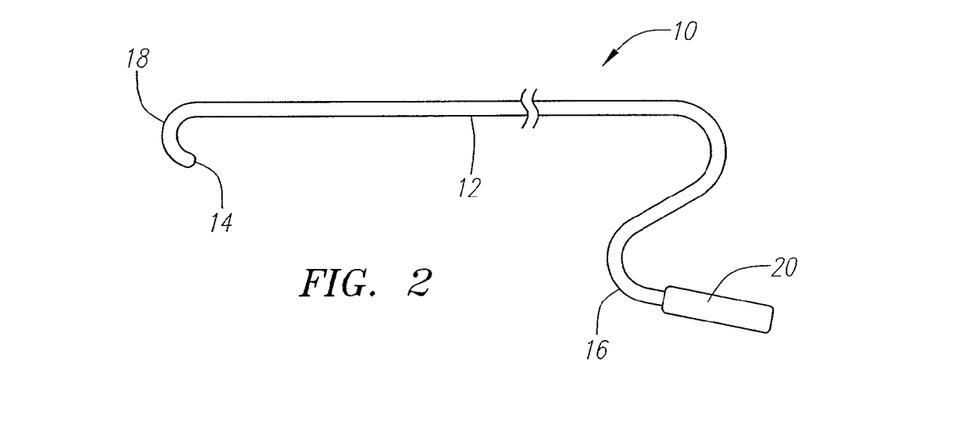
FIG. 2 is a plan view of a variation of the catheter of FIG. 1, particularly showing the distal end of the elongated member having a J-shaped relaxed configuration.
Figure 3:
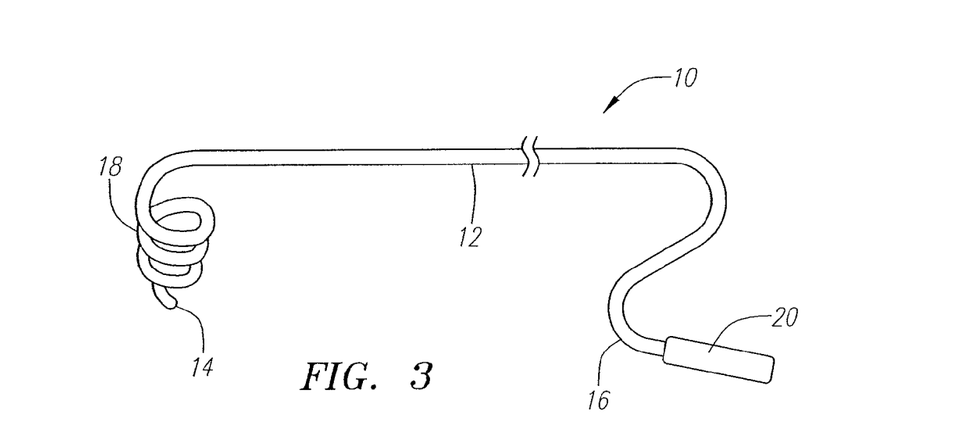
FIG. 3 is a plan view of a variation of the catheter of FIG. 1, particularly showing the distal end of the elongated member having a tapered spiral relaxed configuration.

As shown in FIG. 1, the distal end 18 of the catheter body 12 is straight (i.e., substantially rectilinear). Alternatively, the distal end 18 of the catheter body 12 may be bent or pre-formed into a variety of shapes. FIG. 2 is a variation of the catheter 10 of FIG. 1, which has pre-shaped curvilinear distal end 18 having a J-shape. FIG. 3 is another variation of the catheter 10 of FIG. 1, which has a tapered spiral shaped distal end 18. It should be noted that the distal end 18 of the catheter body 12 may have other shapes as well, which will depend on the particular application. The geometry of the catheter body 12 can be created by thermo-forming it into the desired shape. Alternatively, the body of the catheter body 12 can include an interior core of super-elastic material, like Nitinol® wire, that is itself preshaped into the desired configuration and is placed within a soft tubing.

The catheter body 12 preferably has a cross-sectional geometry that is circular. However, other cross-sectional shapes, such as elliptical, rectangular, triangular, and various customized shapes, may be used as well. The catheter body 12 is preferably preformed of an inert, resilient plastic material that retains its shape and does not soften significantly at body temperature, like Pebax®, polyethylene, or Hytrel® (polyester). Alternatively, the catheter body 12 may be made of a variety of materials, including, but not limited to, metals and polymers. The catheter body 12 is preferably flexible so that it is capable of winding through a tortuous path that leads to a target site, i.e., an area within the heart. Alternatively, the catheter body 12 may be semi-rigid, i.e., by being made of a stiff material, or by being reinforced with a coating or coil, to limit the amount of flexing. The stiffness or flexibility of the catheter body 12 is a matter of design choice, and will depend on the particular application. The outer diameter of the catheter body 12 is preferably less than 0.118 inch (9F). However, other dimensions for the outer diameter of the catheter body 12 may also be appropriate, depending on the particular application or clinical procedure.

Figure 4:
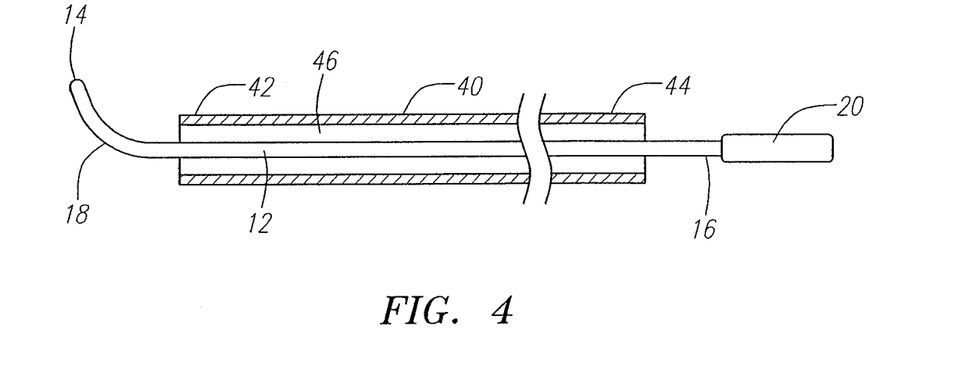
FIG. 4 is a plan view of an alternative embodiment of the catheter, particularly showing the catheter having a tubular element.
Figure 5:
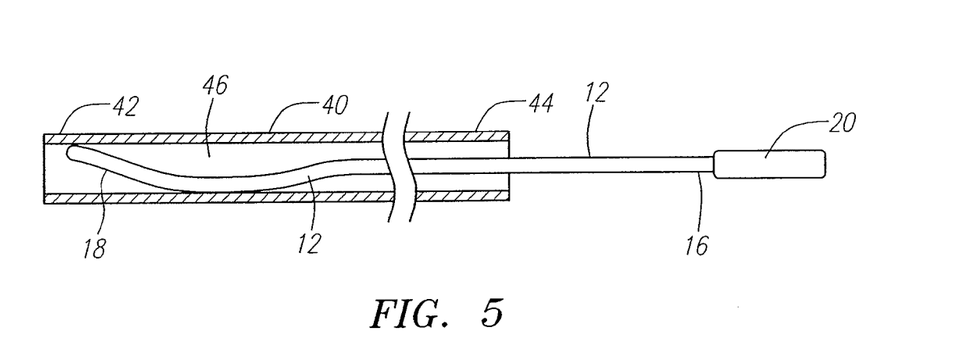
FIG. 5 is a plan view of the catheter of FIG. 4, particularly showing the distal end of the elongated member being stretched within the lumen of the tubular element.

The catheter 10 may optionally be used with a sheath 40 as shown in FIG. 4. The sheath 40 includes a distal end 42, a proximal end 44, and a lumen 46 extending between the distal end 42 and the proximal end 44. The sheath 40 coaxially surrounds a portion of the catheter body 12, such that the distal end 18 of the catheter body 12 can be positioned in and out of the lumen 46 at the distal end 42 of the sheath 40. FIG. 4 shows the distal end 18 (having curvilinear relaxed configuration) of the catheter body 12 outside the lumen 46 of the sheath 40. When outside the lumen 46 of the sheath 40, the distal end 18 of the catheter body 12 is un-restrained by the sheath 40. As such, the distal end 18 of the catheter body 12 is free to assume its relaxed curvilinear configuration. When the distal end 18 of the catheter body 12 is retracted into the lumen 46 of the sheath 40, as shown in FIG. 5, the distal end 18 of the catheter body 12 is stretched into a configuration that has a relatively low cross-sectional profile.

Figure 6:
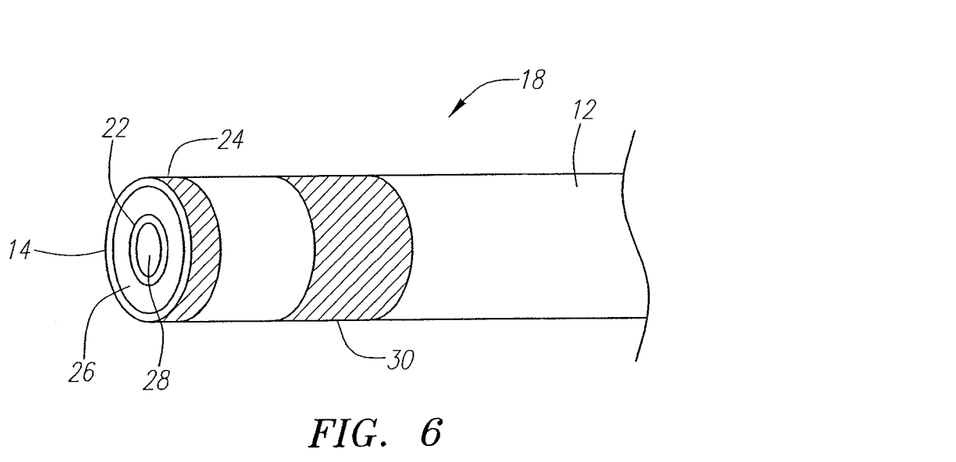
FIG. 6 is a front perspective view of the distal end of the catheter in FIG. 1, particularly showing the first ring electrode and the second ring electrode at the distal tip of the catheter in accordance with a first aspect of the present invention.

Referring to FIG. 6, the second ring electrode 24 is located substantially concentric to the first ring electrode 22, and is coaxially surrounding the first ring electrode 22. An insulative material 26 which is disposed within the annular space between the ring electrodes 22 and 24, is used to electrically insulate the first ring electrode 22 from the second ring electrode 24. As will be described in further detail below, a portion of the catheter tip 14 can serve as the insulative material 26. The catheter 10 optionally includes one or more additional electrodes 30 carried by the distal end 18 of the catheter body 12 proximal to the ring electrodes 22 and 24.

In the illustrated embodiment, the ring electrodes 22 and 24 have outer diameters of 0.052 inch and 0.092 inch, respectively. In particular, the outer diameter of the second ring electrode 24 should be about the same as that of the catheter body 12 so that the catheter body 12 exhibits a uniform diameter along its length. The ring electrodes 22 and 24 may have outer diameters with other dimensions as well. As shown in FIG. 6, the ring electrodes 22 and 24 are substantially cylindrical. Alternatively, the ring electrodes 22 and 24 can have other geometric cross-sectional shapes, such as elliptical, rectangular, trianglular, or other customized shapes. Furthermore, the first ring electrode 22 may have a cross-sectional shape that is different from that of the second ring electrode 24. The ring electrodes 22 and 24 can be made of a solid, electrically conducting material, such as, e.g., platinum or gold, that is attached about the catheter tip 14 of the catheter body 12. Alternatively, the ring electrodes 22 and 24 can be formed by coating the tip 14 of the catheter body 12 with an electrically conducting material, such as, e.g., platinum or gold. The coating can be applied using sputtering, ion beam deposition, or equivalent techniques. The additional electrode(s) 30 can be formed using similar materials and techniques.

The advantage of having concentric ring electrodes 22 and 24 over the ring-eye electrode configuration is that the concentric ring configuration is capable of detecting electrical activity with more precise resolution when used during the mapping function. In particular, the thin profile of the ring electrode 22 contacts less tissue surface area, and therefore, allows measurement of electrical activity at a more focused tissue area. The profile of the ring electrode 22 also reduces the averaging of electrical signal measurements, which commonly happens for eye electrodes. As such, the concentric ring electrode configuration allows a physician to accurately determine a target site to be ablated, which in turn reduces operation time and unnecessary tissue ablation. The concentric ring configuration is believed to also reduce the detection of far field electrical activity which can negatively affect the detection of local electrical activity.

Figure 7A:
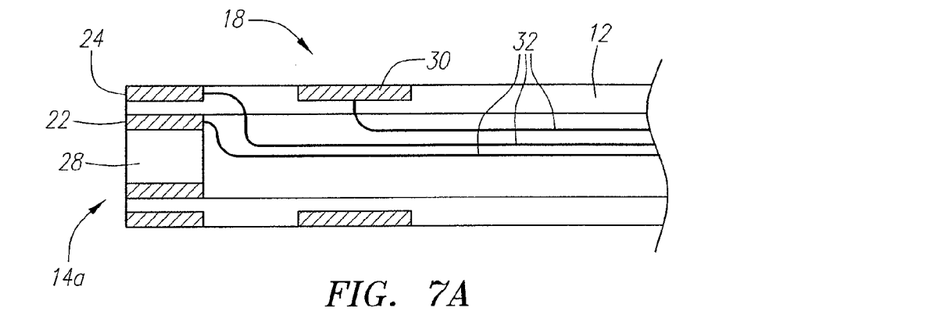
FIG. 7A is a cross-sectional side view of the distal end of the catheter in accordance with a preferred embodiment of the present invention.
Figure 7B:
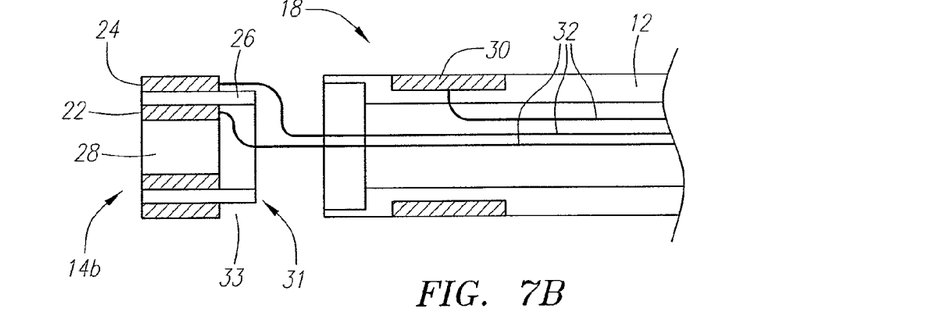
FIG. 7B is a cross-sectional side view of a variation of the distal end of the catheter, particularly showing the catheter tip being fabricated separately from the elongated member.

Referring to FIGS. 7A-7E, the catheter tip 14 may be variously formed onto the catheter body 12. For example, as illustrated in FIG. 7A, a catheter tip 14a is shown as being a part of the catheter body 12 that is fabricated together with the catheter body 12 to form a unibody design. Alternatively, as shown in FIG. 7B, a catheter tip 14b may be separately fabricated from the catheter body 12. In this case, the catheter tip 14b is secured to the distal end 18 of the catheter body 12 during the manufacturing process or by a physician or assistant just prior to treatment. The catheter tip 14b includes a proximal end 33 that is designed to mate with the distal end 18 of the catheter body 12. For example, the catheter tip 14b may be secured to the catheter body 12 by an adhesive, such as weld, glue, or solder, depending on the materials from which the proximal end 33 of the catheter tip 14b and the catheter body 12 are made. Alternatively, the catheter tip 14b may be secured to the catheter body 12 by other mechanisms, such as screws, luer-type connection, or frictional-type connection, which are commonly known to those skilled in the art.

Figure 7C:
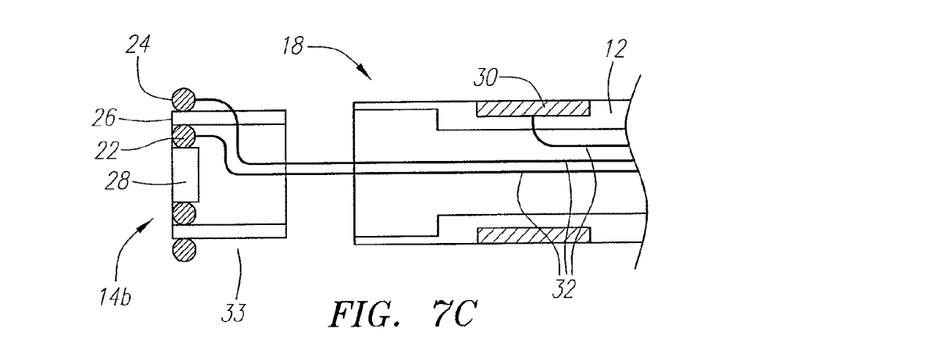
FIG. 7C is a cross-sectional side view of a variation of the catheter tip, particularly showing the first ring electrode and the second ring electrode having a circular cross-sectional shape.

As shown in FIG. 7A or 7B, the cross-sectional profiles of the ring electrodes 22 and 24 are rectangular. Alternatively, as shown in FIG. 7C, the cross-sectional profile for each of the ring electrodes 22 and 24 can exhibit other shapes, such as a circular shape. As illustrated, the body of the catheter tip 14b serves as the insulative 26 whether it forms a unibody design with the catheter body 12 (FIG. 7A) or is formed separately from the catheter body 12 (FIG. 7B). In this case, the insulative material 26 will be formed of the same material as the catheter tip 14. In any event, the insulative material 26 is preferably a polymer, such as PEBAX, urethane, or nylon, but can include other electrically non-conductive materials. To provide precise measurement of electrical signals at local heart tissues with superior resolution, the thickness 31 of the insulative material 26 is preferably between 0.02 inch (0.5 mm) to 0.040 inch (1.0 mm). However, the insulative material 26 can be of any other thickness, depending on the specific application. The bore of the first ring electrode 22 is optionally be occupied with an insulative material 28. The insulative material 28 may be any of a variety of materials, such as a polymer, or any other suitable material. However, any of the materials discussed previously with reference to the insulative material 26 is also applicable for the insulative material 28.

In the illustrated embodiment, each of the ring electrodes 22 and 24 is electrically coupled to one wire 32. Alternatively, each of the ring electrodes 22 and 24 can be electrically coupled to two spaced apart wires 32 for delivering power in parallel to each of the ring electrodes 22 and 24. This decreases the effect of voltage gradients within each of the ring electrodes 22 and 24, which in turn improves the uniformity of current density delivered by the ring electrodes 22 and 24. The wires 32 for conducting ablation energy to the ring electrodes 22 and 24 are also used to transmit signals sensed by the respective ring electrodes 22 and 24 when the catheter 10 is being used to map heart tissue. Alternatively, a separate wire coupled to each of the respective ring electrodes 22 and 24 may be used to transmit sensed signals.

Figure 7D:
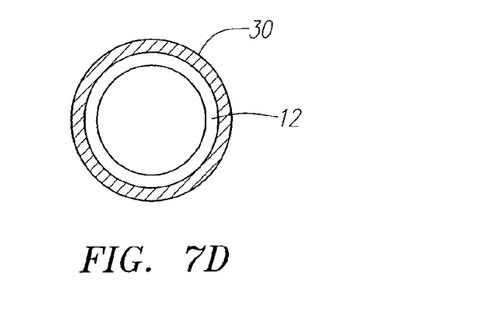
FIG. 7D is a cross-sectional view of the elongated member, particularly showing the additional electrode having a shape of a complete ring.
Figure 7E:
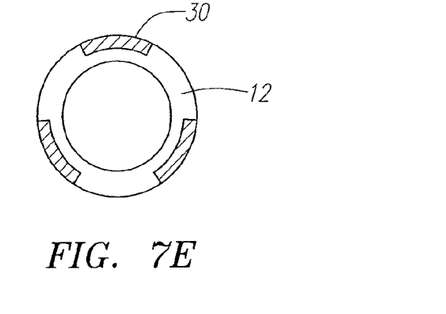
FIG. 7E is a cross-sectional view of the elongated member, particularly showing the additional electrode having a shape of a partial ring.

The additional electrode 30 shown in FIGS. 7A-7C is preferably cylindrical in shape, and is coaxially secured about the circumference of the catheter body 12. FIG. 7D is a cross sectional view of the catheter body 12, which shows the electrode 30 coaxially secured to the circumference of the elongated member. Alternatively, as illustrated in FIG. 7E, the electrode 30 can be a partial ring that is secured to a surface of the catheter body 12. FIG. 7E shows the three electrodes 30 spaced uniformly around the circumference of the catheter body 12. The additional electrode 30 can be used for ablation and/or measuring electrical signals at a target site within the heart. The additional electrode 30 can also be used for navigation of the distal end 18 of the catheter body 12, and/or ablation of biological tissues. The spacing between the additional electrode 30 and the ring electrodes 22 and 24 may vary, depending on the requirements of a particular application. In a representative embodiment, the additional electrode 30 is 0.08 inch (2 mm) to 0.197 inch (5 mm) from the ring electrodes 22 and 24. The additional electrode 30 is electrically coupled to a wire for conducting ablating energy and/or electrical signals, as described previously with respect to the ring electrodes 22 and 24. Further details on additional ring electrodes are disclosed in U.S. Pat. No. 5,582,609, the entirety of which is incorporated by reference herein.

Figure 8A:
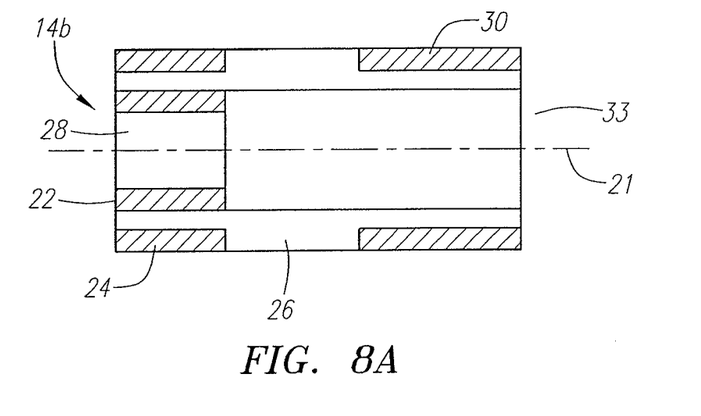
FIG. 8A is a cross-sectional side view of a variation of the catheter tip, particularly showing the catheter tip having an additional electrode.
Figure 8B:
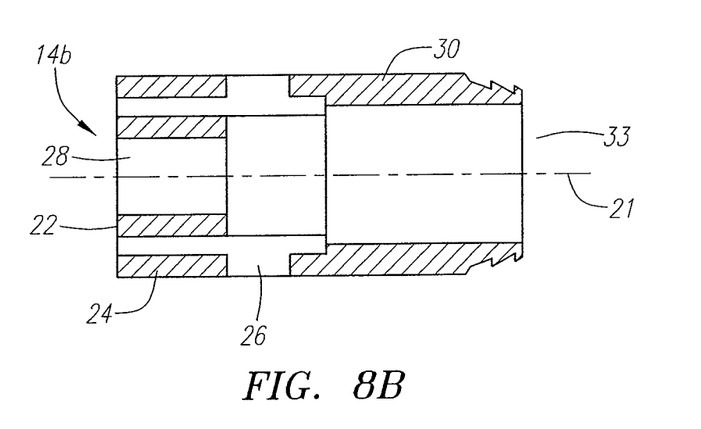
FIG. 8B is a cross-sectional side view of a variation of the catheter tip, particularly showing the proximal end of the catheter tip having a luer-type connection.

The previous embodiments show that an additional electrode 30 may optionally be secured to the catheter body 12. Alternatively, in the case where the distal tip is separate from the elongate member 12, the electrode 30 may be secured to the catheter tip 14. FIG. 8A illustrates a variation of the catheter tip 14b of the catheter 10, which includes the additional electrode 30 as described previously. The insulative material 26 provides electrical insulation between the ring electrodes 22 and 24, and between the second ring electrode 24 and the additional electrode 30. As discussed previously, each of the electrodes is electrically coupled to at least a wire 32. The proximal end 33 of the catheter tip 14b is designed to mate with the distal end 18 of the catheter body 12. For example, as shown in FIG. 8B, the proximal end 33 of the electrode 30 can be fabricated or molded to have threads so that the proximal end 33 of the catheter tip 14b has a luer-type connection for securing the catheter tip 14 to the catheter body 12.

Figure 8C:
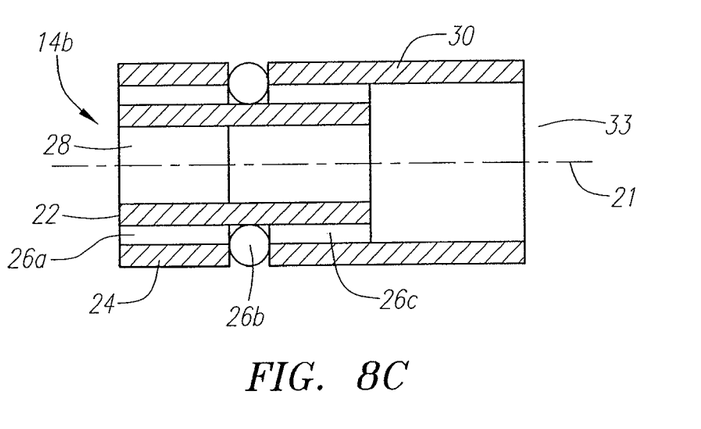
FIG. 8C is a cross-sectional side view of the catheter tip, particularly showing the insulative material in the form of an O-ring.

As shown previously, the single insulative material 26 provides the insulation function among all the electrodes at the catheter tip 14. Alternatively, more than one insulative material may be used to provide insulation among the electrodes. FIG. 8C shows a variation of the catheter tip 14 of FIG. 8A, which includes three insulative materials 26a, 26b, and 26c. Insulative material 26a provides electrical insulation between the ring electrodes 22 and 24. Insulative material 26b provides electrical insulation between the second ring electrode 24 and the additional electrode 30. Insulative material 26c provides electrical insulation between the additional electrode 30 and the first ring electrode 22. The insulative materials 26a, 26b, and 26c are preferably made of the same material. As shown in FIG. 8C, the insulative material 26b is in a form of an O-ring that has a substantially circular cross-section. However, the insulative material 26b can also be an O-ring having other cross-sectional profiles. Similarly, the insulative materials 26a and 26c can have other cross-sectional profiles.

Figure 9:
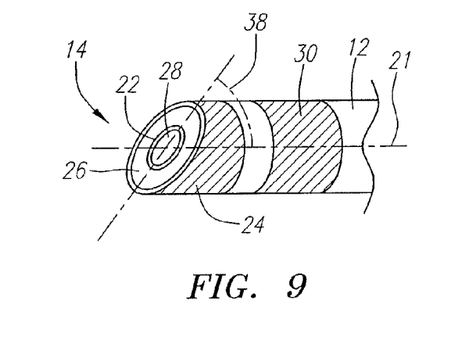
FIG. 9 is a front perspective view of a variation of the distal end of the catheter, particularly showing the distal ends of the first ring electrode and the second ring electrode forming a planar surface at an angle relative to an axis of the elongated member.
Figure 10:
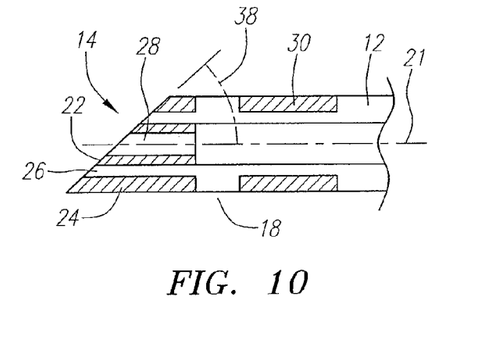
FIG. 10 is a cross-sectional side view of the distal end of FIG. 9.
Figure 11A:
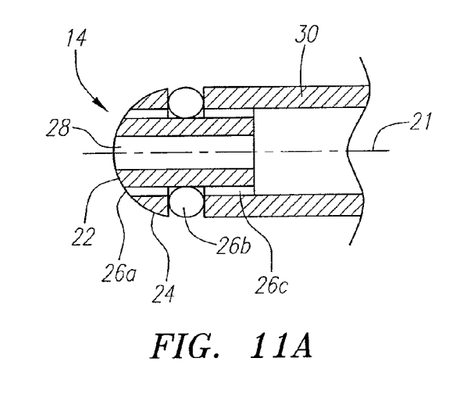
FIG. 11 is a cross-sectional side view of a variation of the distal end of the catheter, particularly showing the distal ends of the first ring electrode and the second ring electrode forming a non-planar surface.
Figure 11B:
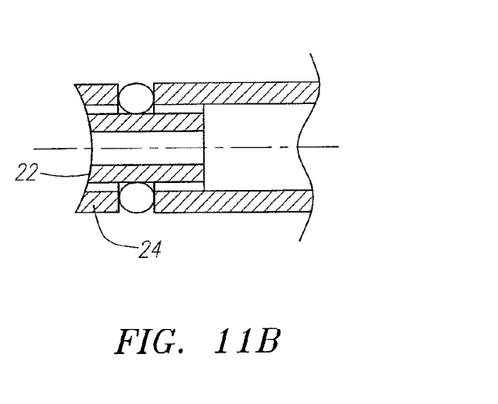

For all the distal tips 14 described previously, the distal ends of the ring electrodes 22 and 24 form a plane that is substantially perpendicular to an axis 21 of the catheter tip 14. However, for any of the distal tips 14 described previously, the plane formed by the distal ends of the ring electrodes 22 and 24 can be of any angle with respect to the axis 21 of the catheter tip 14. For example, as illustrated in FIGS. 9 and 10, the distal ends of the ring electrodes 22 and 24 form a plane that has an angle 38 with respect to the axis 21 of the catheter tip 14. Furthermore, the ring electrodes 22 and 24 can form a non-planar surface. For example, as illustrated in FIG. 11, the distal ends of the ring electrodes 22 and 24 form a non-planar surface. The non-planar surface can be, e.g., a convex surface or a concave surface. The non-planar surface of the catheter tip 14 of FIG. 11 has a parabolic shape. Alternatively, the non-planar surface of the catheter tip 14 can have other profiles or customized shapes.

Figure 12A:
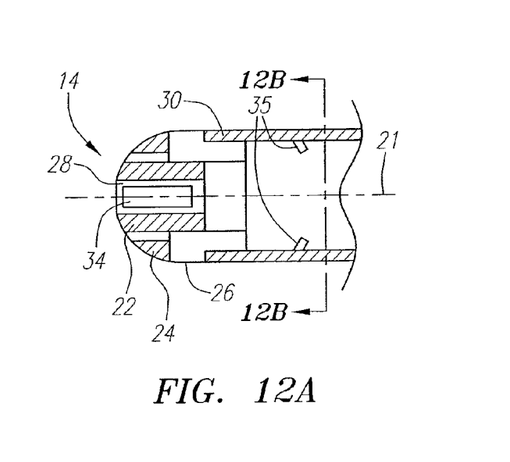
FIG. 12A is a cross-sectional side view of a distal end of a catheter, particularly showing a sensor located within the bore of the ring electrode.
Figure 12B:
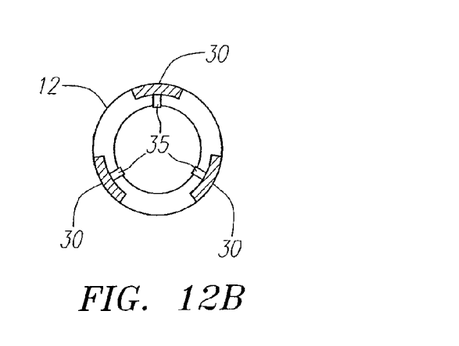
FIG. 12B is a cross-sectional view of a catheter of FIG. 12A.

Any of the previously described distal tips 14 can optionally include a sensor 34, such as that shown in FIG. 12A. The sensor 34 can be a thermal sensor such as a thermistor or a thermocouple, for sensing a temperature. Thermal sensors are described in the U.S. Pat. No. 5,582,609, and U.S. patent application Ser. No. 08/286,930, filed on Aug. 8, 1994, both of which are incorporated by reference herein. The sensor 34 may also comprises other types of sensors that measure characteristics of body tissue, such as a current sensor, an impedance sensor, or pressure sensor. The sensor 34 is preferably embedded within the insulative material 28 within the bore of the ring electrode 22. Alternatively, the sensor 34 may be secured to the catheter tip 14 by an adhesive, such as a weld, or other securing mechanisms, such as screws. As shown in the illustrated embodiment, the ring electrode 22 allows the sensor 34 to be placed adjacent to or directly against a tissue, thereby increasing the measurements of the sensor 34. It should be noted that besides the ring electrode 22, each of the additional electrodes 30 described previously can optionally carry a sensor 35, as shown in FIGS. 12A and 12B. The sensor 35 is preferably a thermistor. However, other types of sensors discussed previously with reference to the sensor 34 may also be used for the sensor 35.

Figure 13A:
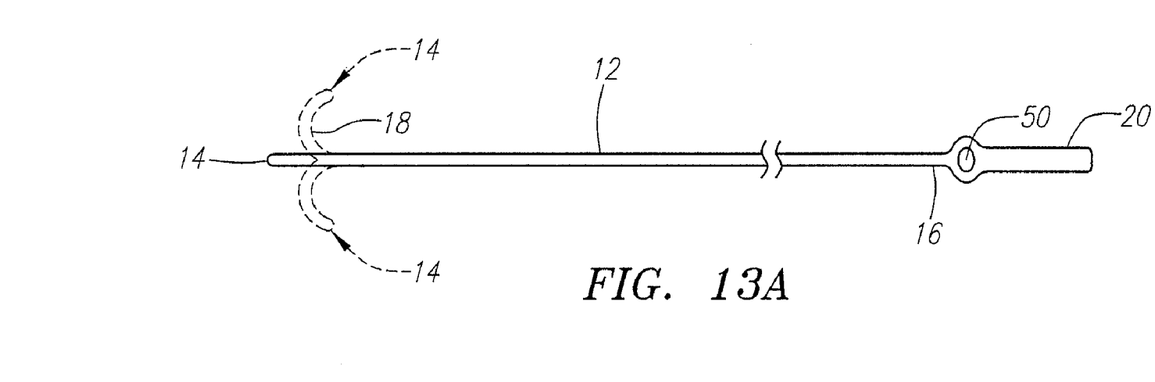
FIG. 13A is a plan view of an alternative embodiment of the catheter of FIG. 1, particularly showing the distal end of the elongated member being steerable.
Figure 13B:
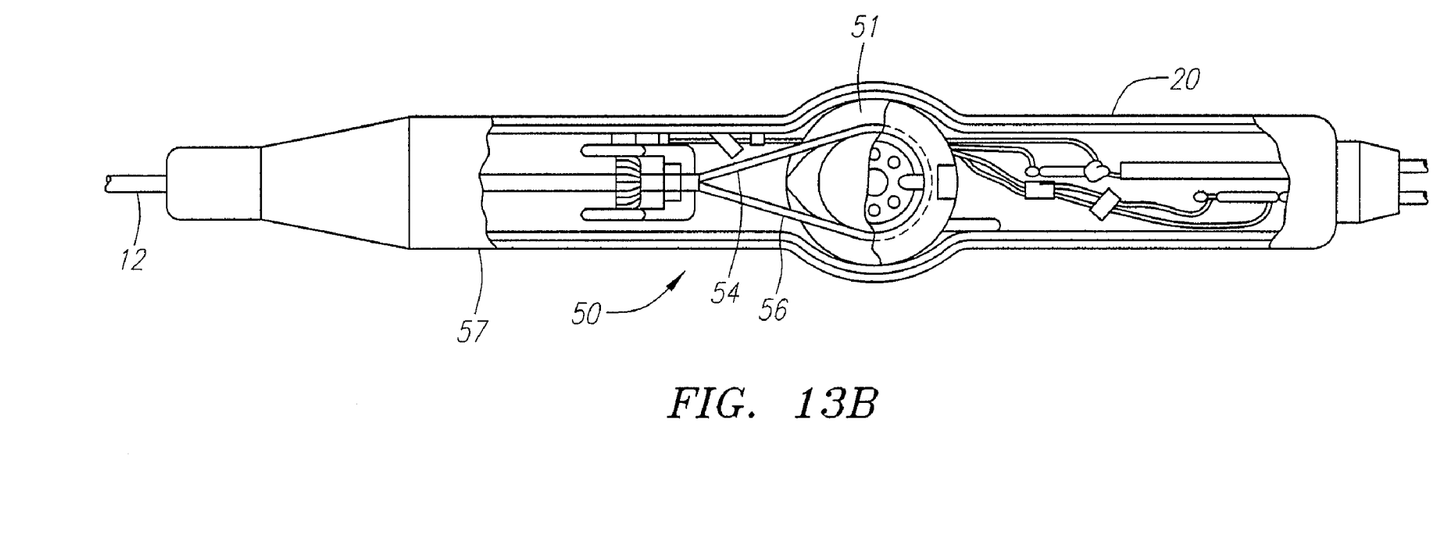
FIG. 13B is a plan view of the steering mechanism of FIG. 13A.

Turning to FIG. 13A, the handle 20 of the catheter 10 of FIG. 1 may optionally include a steering mechanism 50 for changing the shape of the distal end 18 of the catheter body 12. The steering mechanism 50 can vary. In the illustrated embodiment (see FIG. 13B), the steering mechanism is the one shown in U.S. Pat. No. 5,363,861 issued Nov. 15, 1994, which is incorporated by reference herein. As FIG. 13B shows, the steering mechanism 50 includes a rotating cam wheel 51 within the handle 20. An external steering lever or control (not shown) rotates the cam wheel 51. The cam wheel 51 holds the proximal ends of right and left steering wires 54 and 56, which extend along the associated left and right side surfaces of the cam wheel 51 and through a guide tube 57. The steering wires 54 and 56 connect to the left and right sides of a resilient bendable wire or spring within a distal section of the elongate member 12. Alternatively, the steering wires 54 and 56 may connect to the catheter tip 14 or an inner surface of the catheter body 12 at the distal end 18.

As FIG. 13A shows, manipulating the steering lever or control causes the distal end 18 of the catheter body 12 to bend up or down. By rotating the handle, thereby rotating the distal end 18 of the catheter body 12, and by manipulating the steering lever, it is possible to maneuver the distal end 18 of the catheter body 12 virtually in any direction. The steerable section simplifies the positioning of the distal end 18 of the catheter 10 within the heart.

Figure 14:
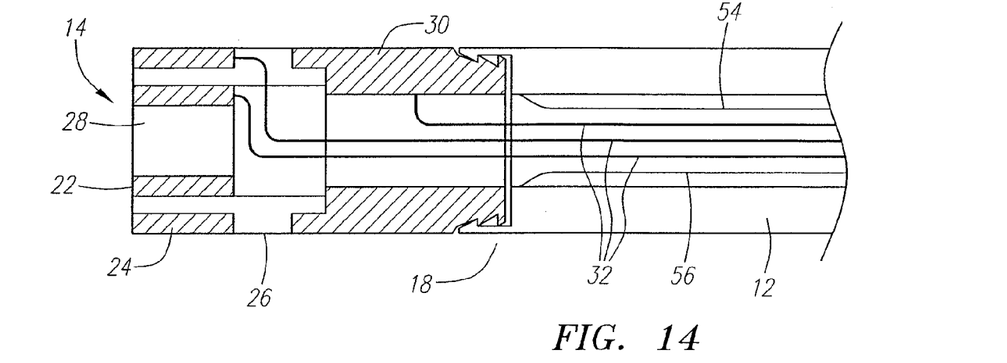
FIG. 14 is a cross-sectional top view of the distal end of the catheter of FIG. 13A, particularly showing the steering wires connected to the body of the elongated member.
Figure 15:
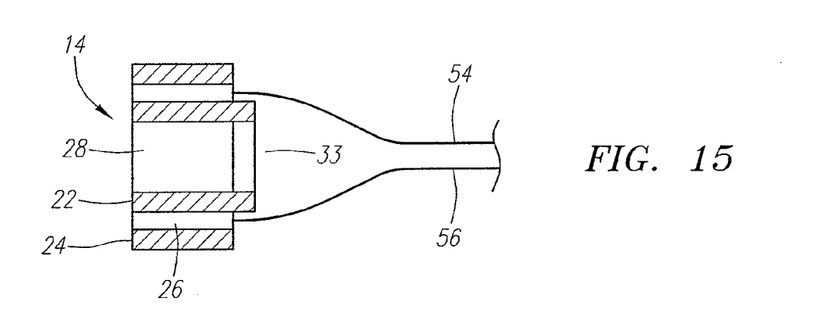
FIG. 15 is a cross-sectional top view of a variation of the distal end of the catheter of FIG. 13A, particularly showing the steering wires connected to the insulative material at the distal end of the elongated member.
Figure 16A:
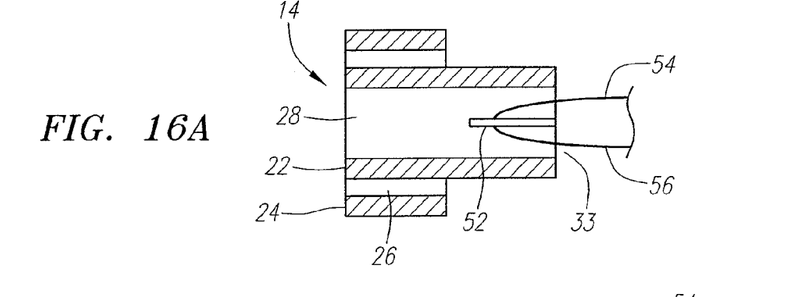
FIG. 16A is a cross-sectional top view of the distal end of the catheter of FIG. 13A, particularly showing the steering wires connected to a member located within the bore of the first ring electrode.
Figure 16B:
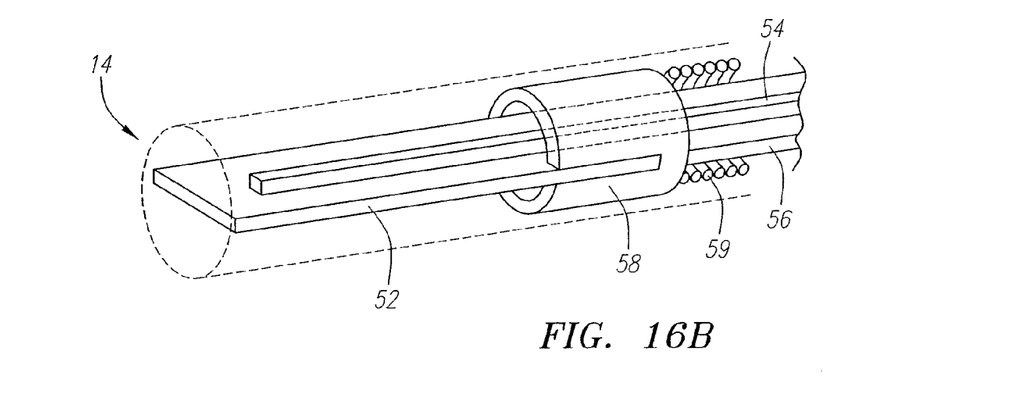
FIG. 16B is a perspective view of a variation of the member of FIG. 16A.

As illustrated in FIG. 14, the distal end of each of the steering wires 54 and 56 is secured to the distal end 18 of the catheter body 12. Alternatively, the distal end of each of the steering wires 54 and 56 can be secured to the catheter tip 14. For example, as illustrated in FIG. 15, the distal ends of the steering wires 54 and 56 are secured to the insulative material 26 of the catheter tip 14. As illustrated in FIG. 16A, the distal ends of the steering wires 54 and 56 are secured to an element 52 located within the bore of the first ring electrode 22. The element 52, which can be a wire or a plate, is preferably made of an elastic material that is embedded within the insulative material 28, or secured to the insulative material 28 by an adhesive or connection. Alternatively, as shown in FIG. 16B, the element 52 can be secured to a ferrule 58, which in turn, is coaxially secured within the catheter body 12. A coil spring 59 may optionally be included for strengthening and/or stiffening the catheter body 12.

It should be noted that the steering mechanism is not limited to the illustrative examples described previously, and that other steering mechanisms known in the art may also be used. Steering mechanisms are described in U.S. Pat. Nos. 6,033,378, 5,891,088, 5,531,686, 5,456,664, and 5,395,327. The entirety of these patents is incorporated by reference herein.

Having described the detailed structure of the catheter 10, the details of its operation will now be described. When using the catheter 10 to diagnose or treat a heart, the physician first establishes an access to a selected vein or artery. A conventional introducer may be used to penetrate a patient's skin and establish the access. If the catheter 10 includes a sheath 40, such as that shown in FIG. 4, the catheter body 12 is first positioned such that the distal end 18 of the catheter body 12 is coaxially surrounded within the distal end 42 of the sheath 40. The sheath 40, together with the catheter body 12, are then inserted into the selected vein or artery. Alternatively, catheter body 12 the sheath 40 and catheter 10 are introduced separately. Specifically, the sheath 40 is first introduced into the selected vein or artery. A guidewire may be used to facilitate the insertion of the sheath 40 in a conventional manner. Once the sheath 40 is in place, the catheter body 12 is then inserted into the lumen 46 of the sheath 40. The distal end 18 of the catheter body 12 is then advanced progressively until it reaches a target site within the heart.

The physician can use angioscopic, fluoroscopic, or ultrasound imaging, or the like, to observe the distal end 18 of the catheter body 12 while maneuvering it into good contact with an endocardial tissue. If fluoroscopic imaging is used, either or both of the sheath 40 and the catheter body 12 can include a radio-opaque compound, such as barium sulfate, to assist in the positioning of the sheath 40 and the catheter body 12 during a fluoroscopic procedure. Alternatively, a radio-opaque marker can be placed at either or both of the distal ends of the sheath 40 and the catheter body 12 for this purpose. A marker may also be placed at the proximal end 16 of the catheter body 12 or at the handle 20 for indicating the orientation of the distal end 18 of the catheter body 12. Alternatively, any of the ring electrodes 22 and 24 and the additional electrode 30 can assist the navigation of the distal end 18 of the catheter body 12 by emitting and/or sensing a radio frequency signal. Navigation systems that use signal emitting and signal sensing electrodes are described in U.S. patent application Ser. No. 09/624,358, filed on Jul. 24, 2000, the entirety of which is incorporated by reference herein. Furthermore, the catheter body 12 can also carry an ultrasound or magnetic transmitter/sensor for navigating the distal end 18, as is known in the art.

Figure 17:
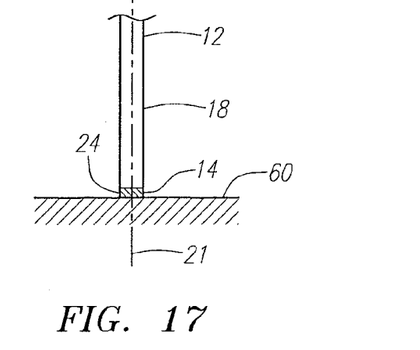
FIG. 17 is a side view of the distal end of the catheter, particularly showing the catheter tip being in contact with a tissue.

Turning to FIG. 17, when using the catheter device 10 for mapping heart tissue, the catheter tip 14 is placed in contact with the heart tissue 60. In particular, at least one of the ring electrodes 22 and 24 at the catheter tip 14 should be in contact with the surface of the heart tissue 60. Preferably, both of the ring electrodes 22 and 24 are placed in contact with the heart tissue 60 at a location where a measurement of electrical activity is desired. Although electrical measurements can be obtained by placing a single ring electrode in contact with the heart tissue 60, having both the ring electrodes 22 and 24 in contact with the heart tissue 60 has the benefit of obtaining more precise measurements. If the distal end 18 of the catheter body 12 has a non-linear relaxed configuration, the distal end 18 will resume its relaxed configuration once it is outside the distal end 42 of the sheath 40. The physician can then change the position of the distal end 18 of the catheter body 12 by manipulating the proximal end 16 of the catheter body 12, or the handle 20 if one is provided. If the catheter 10 includes a steering mechanism 50, it can be used to position the distal end 18 of the catheter body 12 as well.

FIG. 17 shows the catheter tip 14 of FIG. 6, in which the distal ends of the ring electrodes 22 and 24 form a surface that is perpendicular to the axis 21 of the catheter tip 14. When using such an catheter tip 14, the distal end 18 of the catheter body 12 is preferably positioned such that the axis 21 of the catheter tip 14 is substantially perpendicular to the surface of the targeted heart tissue 60. This maximizes the surface of the ring electrodes 22 and 24 that are in contact with the targeted heart tissue 60.

Figure 18:
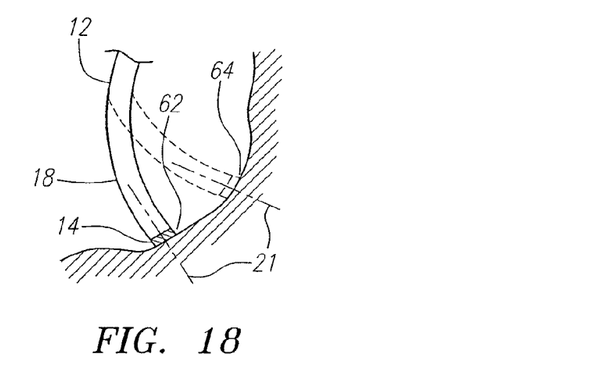
FIG. 18 is a side view of the distal end of the catheter, particularly showing the distal end of the elongated member being steerable.

If it is difficult to place the ring electrodes 22 and 24 in contact with the heart tissue 60 using the straight distal end 18 of FIG. 17, the catheter body 12 having the relaxed curvilinear configuration can be used to assist in the positioning of the catheter tip 14, as illustrated in FIG. 18. Furthermore, if the catheter 10 includes a steering mechanism 50, it can be used to change the curvature of the distal end 18 of the catheter body 12 so that the surface of the catheter tip 14 is substantially parallel to the surface of the heart tissue 60. In FIG. 18, the catheter tip 14 is positioned such that it is in contact with the heart tissue 60 at a position 62. If it is desirable to position the catheter tip 14 to a different location, i.e., position 64, the steering mechanism 50 can be used to steer or change the curvature of the distal end 18 of the catheter device 10, as indicated by the dashed lines, so that both the ring electrodes 22 and 24 at the catheter tip 14 are in contact with the heart tissue at a new location 64.

Figure 19A:
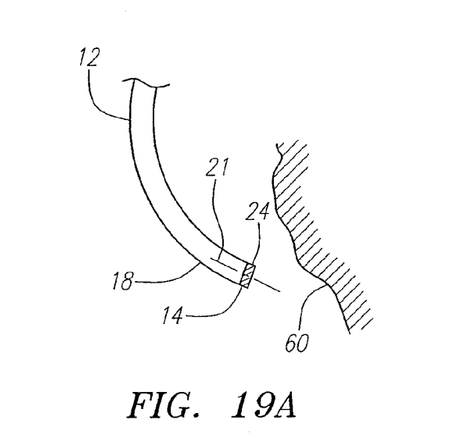
FIG. 19A is a side view of the distal end of the catheter, particularly showing the surface of the catheter tip not being in substantial contact with a tissue.
Figure 19B:
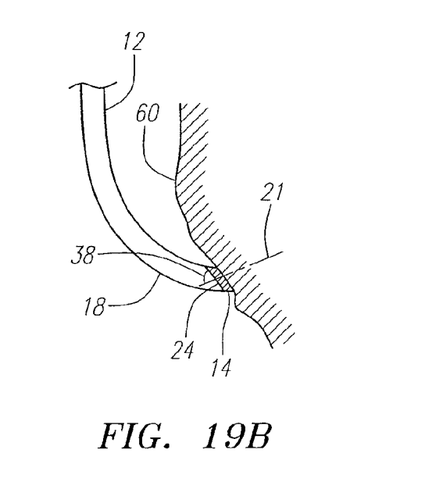
FIG. 19B is a side view of the distal end of the catheter, particularly showing the surface of the catheter tip being in substantial contact with a tissue.

In certain situations, using a distal end 18 of the catheter body 12 that has a relaxed curvilinear configuration or is steerable may not be sufficient for the catheter tip 14 to make substantial contact with a target tissue. FIG. 19A shows the catheter tip 14 having a surface that is substantially perpendicular to the axis 21 of the catheter tip 14. The catheter tip 14 is steered to make contact with a targeted heart tissue. However, because of the limited flexibility of the elongated member and/or the geometry or orientation of the surface of the targeted heart tissue 60, substantial contact between the ring electrodes 22 and 24 and the heart tissue cannot be achieved. In this case, the configuration of the catheter tip 14 having a planar surface that forms an angle 38 relative to the axis 21 of the catheter tip 14 would enable the ring electrodes 22 and 24 to substantially contact the heart tissue 60, as shown in FIG. 19B. Such configuration is particularly useful when it is desirable to map or ablate a heart tissue at a location that is difficult to reach.

Figure 20:
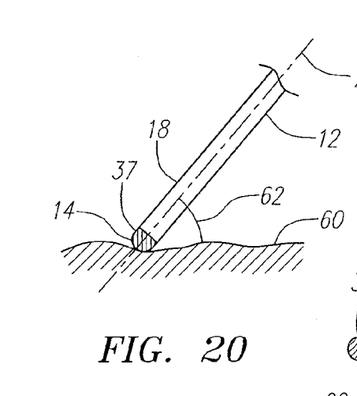
FIG. 20 is a side view of the distal end of the catheter, particularly showing the ring electrode being in contact with a tissue.
Figure 21:
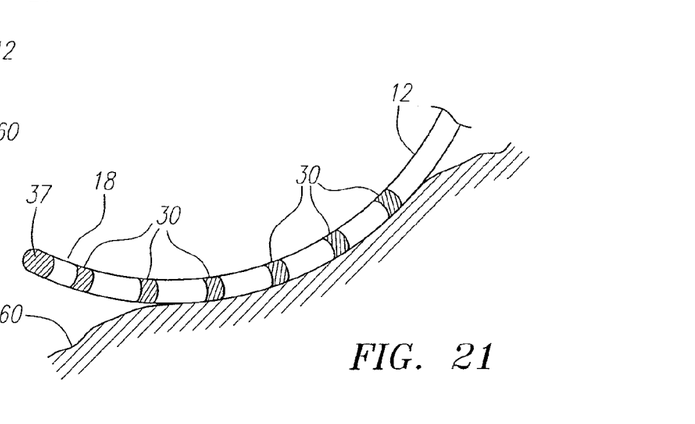
FIG. 21 is a side view of the distal end of the catheter, particularly showing a number of additional electrodes being in contact with the surface of a heart tissue.

Referring to FIG. 20, if the catheter tip 14 has a curvilinear surface, such as that shown in FIG. 11, then the catheter is not required to be positioned such that the axis 21 of the catheter tip 14 is substantially perpendicular to the surface of the heart tissue 60. In this case, the distal end 18 of the catheter body 12 can be positioned at an angle 62 relative to the surface of the heart tissue 60, so long as a portion of either of the ring electrodes 22 and 24 is in contact with the heart tissue 60.

Once proper contact between the ring electrodes 22 and 24 and the heart tissue 60 has been achieved, the mapping process is commenced. During the mapping process, electrical signals sensed by the ring electrodes 22 and 24 are transmitted by the wires 32 to a processor (not shown), such as a computer, a circuit, or a microprocessor. The processor analyzes the signals and converts them to data and/or graphical images on a display, such as a monitor.

At the end of the mapping process, a target site for ablation is then determined. The catheter device 10 can then be used for ablation of a heart tissue 60 at the target site. In the ablation mode, any of the ring electrodes 22 and 24 can be used for ablation. Furthermore, if the catheter 10 includes an additional electrode 30, it can also be used for the mapping and/or ablation. When using the catheter 10 to ablate a target site, the distal end 18 of the catheter body 12 is positioned such that the electrodes (the ring electrodes 22 and 24 and/or the body electrode 30) is in contact with the target site. The distal end 18 of the catheter body 12 can be positioned during the ablation process in the same manner as that used to position the distal end 18 during the mapping process.

While either or both of the ring electrodes 22 and 24 are being used to ablate the heart tissue, the sensor 34 located within the bore of the first ring electrode 22, such as that shown in FIG. 12, may be used to sense a characteristic of the tissue being ablated. If an additional electrode 30 is used to ablate the heart tissue, a sensor 35 located along portions of the elongate body may also be used to sense a characteristic of the tissue being ablated. Based on the sensed characteristic of the tissue being ablated, the sensors 34 and 35 transmit a signal to a processor, which determines the progress of the ablation process. When the ablation process is completed, the catheter body 12 and the sheath 40 are then removed from the patient's body.

Figure 22:
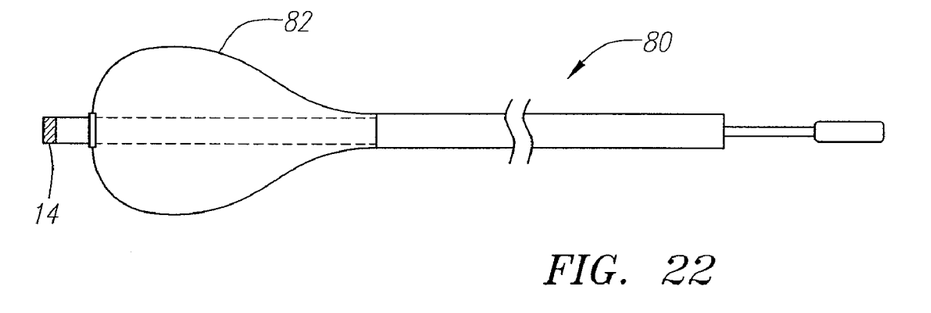
FIG. 22 is a side view of a medical device having an expandable structure.
Figure 23:
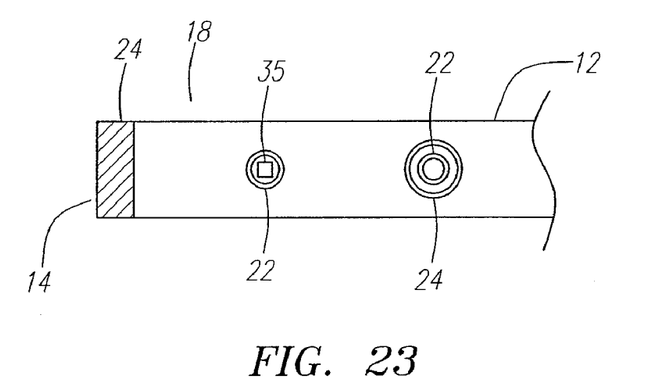
FIG. 23 is a side view of a medical device, particularly showing ring electrodes located along the body of the medical device.

It should be appreciated that the catheter tip 14 is not necessarily limited to being a part of the catheters described herein, and that the catheter tip 14 can be attached to other catheters or medical devices for ablation and/or sensing a signal. FIG. 22 shows the catheter tip 14 being a part of, or connected to, the distal end of a medical device 80 having an expandable structure 82. In addition, the catheter tip 14 can be used in ablation therapy for other areas of the body, and is not necessarily limited to cardiac mapping and ablation. Furthermore, the dual ring electrode configuration of the catheter tip 14 does not have to be employed at the tip 14 of a device. For example, FIG. 23 shows a distal end of a device having a first ring electrode 22 and a second ring electrode 24 located along the body of the device. As such, the ring electrodes 22 and 24 function as body electrodes. FIG. 23 also shows that the additional electrode 30 can optionally include a sensor 35 located within the bore of the ring electrode 22.

Thus, although different embodiments have been shown and described, it would be apparent to those skilled in the art that many changes and modifications may be made thereunto without the departing from the scope of the invention, which is defined by the following claims and their equivalents.

What is claimed is:

1. A medical probe comprising:
   an elongated member having an external lateral surface;
   a first ring electrode mounted to the external lateral surface of the elongated member, such that a longitudinal axis extending perpendicularly through an aperture of the first ring electrode is substantially perpendicular to a longitudinal axis of the elongated member; and
   a second ring electrode mounted to the external lateral surface of the elongated member in a concentric relationship with the first ring electrode, the second ring electrode being electrically insulated from the first ring electrode.

2. The medical probe of claim 1, wherein the first ring electrode and the second ring electrode form an external surface that faces in a direction substantially perpendicular to the longitudinal axis of the elongated member.

3. The medical probe of claim 1, wherein the elongated member has a distal tip, and the first ring electrode is mounted to the elongated member proximal to the distal tip.

4. The medical probe of claim 1, further comprising a thermal sensor mounted on the elongated member.

5. The medical probe of claim 4, wherein the thermal sensor is located coaxially within the first ring electrode.

6. The medical probe of claim 1, wherein the elongate member is a catheter body.

7. The medical probe of claim 1, wherein the first and second ring electrodes are mapping electrodes.

8. A medical system, comprising:
   the medical probe of claim 1; and
   a processor configured for receiving electrical signals sensed by the first and second ring electrodes.

9. The medical system of claim 8, wherein the processor is a mapping processor.

10. A method of using the medical probe of claim 1, comprising:
    placing external surfaces of the first and second ring electrodes in contact with tissue; and
    sensing electrical signals from the tissue by the first and second ring electrodes.

11. The method of claim 10, wherein the tissue is heart tissue.

12. The method of claim 11, further comprising analyzing and converting the electrical signals to graphical data.

13. A method of using the medical probe of claim 5, comprising:
    placing external surfaces of the first and second ring electrodes in contact with tissue;
    sensing electrical signals from the tissue by the first and second ring electrodes; and
    measuring the temperature of the tissue by the thermal sensor.

* * * * *